United States Patent
McGuckin, Jr.

(10) Patent No.: US 8,920,506 B2
(45) Date of Patent: Dec. 30, 2014

(54) SPINAL IMPLANT AND METHOD OF USE

(71) Applicant: James F. McGuckin, Jr., Radnor, PA (US)

(72) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

(21) Appl. No.: 13/631,891

(22) Filed: Sep. 29, 2012

(65) Prior Publication Data

US 2013/0030533 A1   Jan. 31, 2013

Related U.S. Application Data

(60) Continuation of application No. 13/400,414, filed on Feb. 20, 2012, now Pat. No. 8,287,599, which is a division of application No. 11/983,477, filed on Nov. 9, 2007, now Pat. No. 8,142,507.

(60) Provisional application No. 60/859,357, filed on Nov. 16, 2006.

(51) Int. Cl.
*A61F 2/44* (2006.01)
*A61F 2/30* (2006.01)

(52) U.S. Cl.
CPC ............. *A61F 2/441* (2013.01); *A61F 2/442* (2013.01); *A61F 2002/30092* (2013.01);
(Continued)

(58) Field of Classification Search
CPC ..... A61F 2/442; A61F 2/4455; A61F 2/4465; A61F 2/4611; A61F 2002/30579; A61F 2002/30604; A61F 2002/30563; A61F 2002/30624; A61F 2002/30462; A61F 2002/4415; A61F 2002/444; A61F 2002/448; A61F 2002/4627; A61F 2002/30092; A61F 2220/0075; A61F 2230/0091; A61F 2210/0014; A61F 2220/0091; A61F 2002/30136; A61F 2002/30289
USPC ............................................. 623/17.11–17.16
See application file for complete search history.

(56) References Cited

U.S. PATENT DOCUMENTS 3,867,728 A   2/1975 Kahn et al.
4,904,261 A   2/1990 Dove et al.
(Continued)

FOREIGN PATENT DOCUMENTS

DE   19710392 C1 *   7/1999   ............... A61F 2/44
DE   2006/005868   6/2006
(Continued)

*Primary Examiner* — Pedro Philogene
*Assistant Examiner* — Lynnsy Summitt
(74) *Attorney, Agent, or Firm* — Neil D. Gershon

(57) ABSTRACT

A spinal implant having a series of sections or units hinged together and a balloon connected to at least some of the sections, the balloon having a curved configuration. The implant has a first delivery configuration and a second curved placement configuration, wherein it has a more linear configuration in the first delivery configuration than in the second curved configuration. The implant assumes the first delivery configuration during delivery to the disc space and maintains the curved configuration after placement within the disc space. The curved configuration can result from filling or expanding the balloon.

20 Claims, 5 Drawing Sheets

(52) U.S. Cl.
CPC .............. *A61F 2002/30131* (2013.01); *A61F 2002/30378* (2013.01); *A61F 2002/30461* (2013.01); *A61F 2002/30471* (2013.01); *A61F 2002/30579* (2013.01); *A61F 2002/30584* (2013.01); *A61F 2002/30841* (2013.01); *A61F 2002/4415* (2013.01); *A61F 2210/0014* (2013.01); *A61F 2220/0033* (2013.01); *A61F 2220/0075* (2013.01); *A61F 2220/0091* (2013.01); *A61F 2230/0013* (2013.01); *A61F 2310/00017* (2013.01); *A61F 2310/00023* (2013.01); *A61F 2310/00796* (2013.01)
USPC .................... 623/17.16; 623/17.13

(56) References Cited

U.S. PATENT DOCUMENTS

| | | | |
|---|---|---|---|
| 5,578,074 A | 11/1996 | Mirigian | |
| 5,716,416 A | 2/1998 | Lin | |
| 5,749,916 A | 5/1998 | Richelsoph | |
| 5,800,549 A | 9/1998 | Bao et al. | |
| 5,824,093 A | 10/1998 | Ray et al. | |
| 5,830,222 A | 11/1998 | Makower | |
| 5,879,385 A | 3/1999 | Crockard et al. | |
| 5,919,235 A | 7/1999 | Baumgartner et al. | |
| 5,976,187 A | 11/1999 | Richelsoph | |
| 6,117,174 A | 9/2000 | Nolan | |
| 6,127,597 A | 10/2000 | Beyat et al. | |
| 6,132,465 A | 10/2000 | Ray et al. | |
| 6,143,031 A | 11/2000 | Knothe et al. | |
| 6,165,218 A | 12/2000 | Husson et al. | |
| 6,179,875 B1 | 1/2001 | Von Strempel | |
| 6,206,923 B1 | 3/2001 | Boyd et al. | |
| 6,224,630 B1 | 5/2001 | Bao et al. | |
| 6,245,108 B1 | 6/2001 | Biscup | |
| 6,264,695 B1 | 7/2001 | Stoy | |
| 6,280,475 B1 | 8/2001 | Bao et al. | |
| 6,306,170 B2 | 10/2001 | Ray | |
| 6,315,797 B1 | 11/2001 | Middleton | |
| 6,387,130 B1 | 5/2002 | Stone et al. | |
| 6,395,031 B1 | 5/2002 | Foley et al. | |
| 6,402,785 B1 | 6/2002 | Zdeblick et al. | |
| 6,419,705 B1 | 7/2002 | Erickson | |
| 6,432,107 B1 | 8/2002 | Ferree | |
| 6,500,178 B2 | 12/2002 | Zucherman et al. | |
| 6,508,839 B1 | 1/2003 | Lambrecket al. | |
| 6,582,468 B1 | 6/2003 | Gauchet | |
| 6,592,624 B1 | 7/2003 | Fraser et al. | |
| 6,592,625 B2 | 7/2003 | Cauthen | |
| 6,607,557 B1 | 8/2003 | Brosnahan et al. | |
| 6,607,558 B2 | 8/2003 | Kuras | |
| 6,610,094 B2 | 8/2003 | Husson | |
| 6,613,089 B1 | 9/2003 | Estes et al. | |
| 6,613,090 B2 | 9/2003 | Fuss et al. | |
| 6,613,091 B1 | 9/2003 | Zdeblick et al. | |
| 6,626,943 B2 | 9/2003 | Eberlein et al. | |
| 6,645,248 B2 | 11/2003 | Casutt | |
| 6,648,915 B2 | 11/2003 | Sazy | |
| 6,656,224 B2 | 12/2003 | Middleton | |
| 6,669,732 B2 | 12/2003 | Serhan et al. | |
| 6,805,695 B2 | 10/2004 | Keith et al. | |
| 7,018,413 B2 | 3/2006 | Kruger | |
| 7,182,783 B2 | 2/2007 | Trieu | |
| 7,267,690 B2 | 9/2007 | Felt | |
| 7,351,262 B2 | 4/2008 | Bindseil et al. | |
| 7,442,210 B2 | 10/2008 | Segal et al. | |
| 7,491,219 B2 | 2/2009 | Steinberg | |
| 7,591,853 B2 | 9/2009 | Felt et al. | |
| 2001/0010021 A1 | 7/2001 | Boyd et al. | |
| 2002/0026244 A1 | 2/2002 | Trieu | |
| 2002/0077641 A1 | 6/2002 | Michelson | |
| 2002/0077701 A1 | 6/2002 | Kuslich | |
| 2002/0120269 A1 | 8/2002 | Lange | |
| 2002/0173851 A1 | 11/2002 | McKay | |
| 2003/0018390 A1* | 1/2003 | Husson | 623/17.16 |
| 2003/0093154 A1 | 5/2003 | Estes et al. | |
| 2003/0199979 A1 | 10/2003 | McGuckin, Jr. | |
| 2004/0220669 A1* | 11/2004 | Studer | 623/17.12 |
| 2004/0230309 A1 | 11/2004 | DiMauro et al. | |
| 2005/0096745 A1 | 5/2005 | Andre et al. | |
| 2005/0119747 A1 | 6/2005 | Fabris Monterumici et al. | |
| 2005/0131541 A1 | 6/2005 | Trieu | |
| 2006/0041258 A1 | 2/2006 | Galea | |
| 2006/0085002 A1 | 4/2006 | Trieu et al. | |
| 2006/0089646 A1 | 4/2006 | Bonutti | |
| 2006/0106462 A1 | 5/2006 | Tsou | |
| 2006/0173545 A1 | 8/2006 | Cauthen et al. | |
| 2006/0189999 A1 | 8/2006 | Zwirkoski | |
| 2006/0190083 A1 | 8/2006 | Arnin et al. | |
| 2006/0247776 A1 | 11/2006 | Kim | |
| 2006/0247781 A1* | 11/2006 | Francis | 623/17.16 |
| 2006/0247784 A1 | 11/2006 | Kim | |
| 2006/0265077 A1* | 11/2006 | Zwirkoski | 623/17.16 |
| 2006/0287726 A1 | 12/2006 | Segal et al. | |
| 2007/0010889 A1* | 1/2007 | Francis | 623/17.16 |
| 2007/0016298 A1 | 1/2007 | Recoules-Arche et al. | |
| 2007/0055272 A1* | 3/2007 | Schaller | 606/90 |
| 2007/0067035 A1 | 3/2007 | Falahee | |
| 2007/0150064 A1 | 6/2007 | Ruberte et al. | |
| 2007/0162132 A1 | 7/2007 | Messerli | |
| 2007/0191861 A1 | 8/2007 | Allard et al. | |
| 2008/0039942 A1 | 2/2008 | Gergeron | |
| 2008/0058933 A1 | 3/2008 | Garner et al. | |
| 2008/0091269 A1 | 4/2008 | Zipnick et al. | |
| 2008/0125865 A1* | 5/2008 | Abdelgany | 623/17.16 |
| 2008/0221687 A1 | 9/2008 | Viker | |
| 2008/0243249 A1 | 10/2008 | Kohm et al. | |
| 2008/0249628 A1 | 10/2008 | Altarac et al. | |
| 2008/0312743 A1 | 12/2008 | Vila et al. | |
| 2009/0030423 A1 | 1/2009 | Puno | |
| 2009/0171389 A1 | 7/2009 | Sankaran | |
| 2009/0182386 A1 | 7/2009 | Schaller | |
| 2009/0248092 A1 | 10/2009 | Bellas et al. | |
| 2009/0254180 A1 | 10/2009 | Pazanowski et al. | |

FOREIGN PATENT DOCUMENTS

| | | |
|---|---|---|
| EP | 1442715 | 8/2004 |
| WO | WO-0106962 | 2/2001 |
| WO | WO 0112107 | 2/2001 |
| WO | WO-0217824 | 3/2002 |
| WO | WO-03011155 | 2/2003 |

* cited by examiner

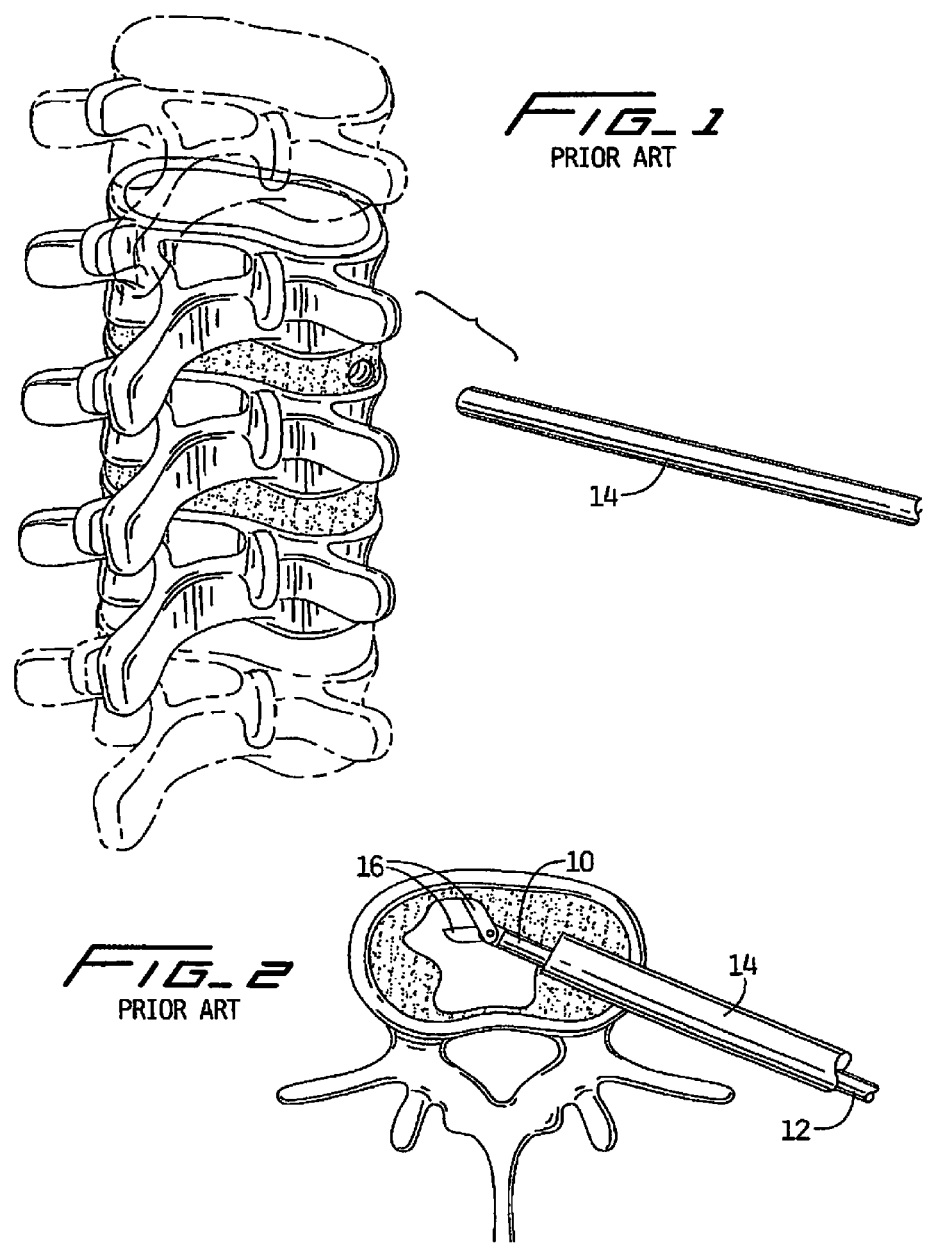

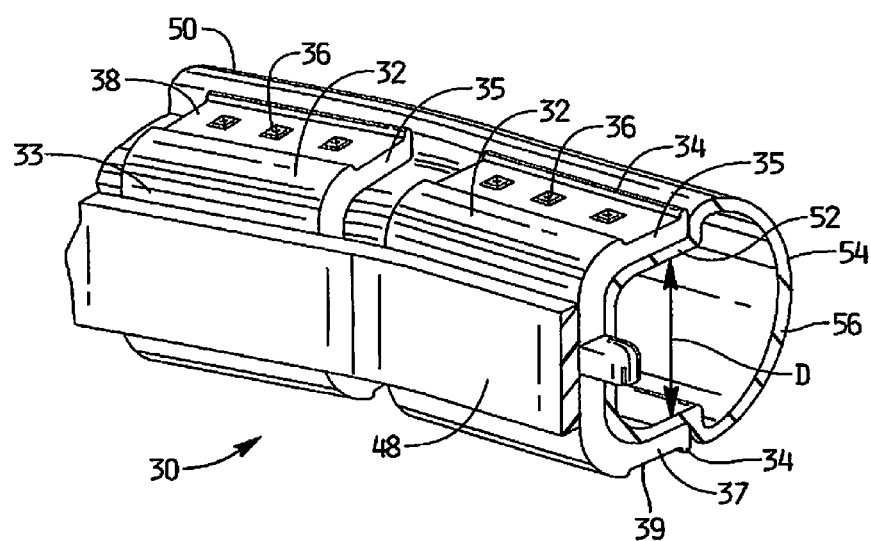
FIG_3
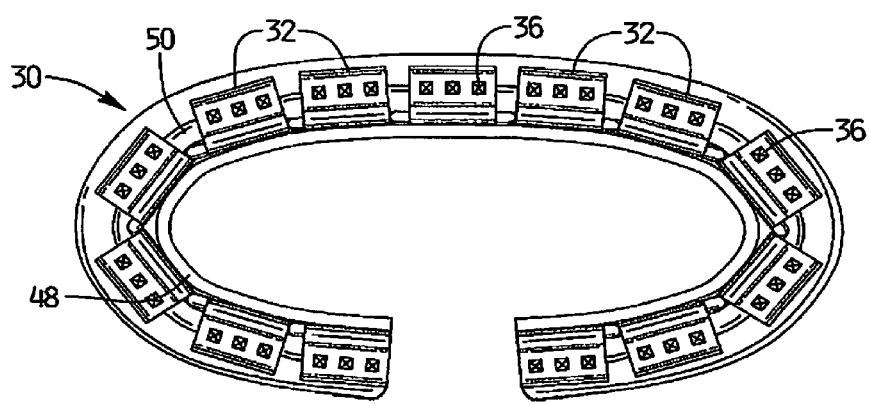
FIG_4

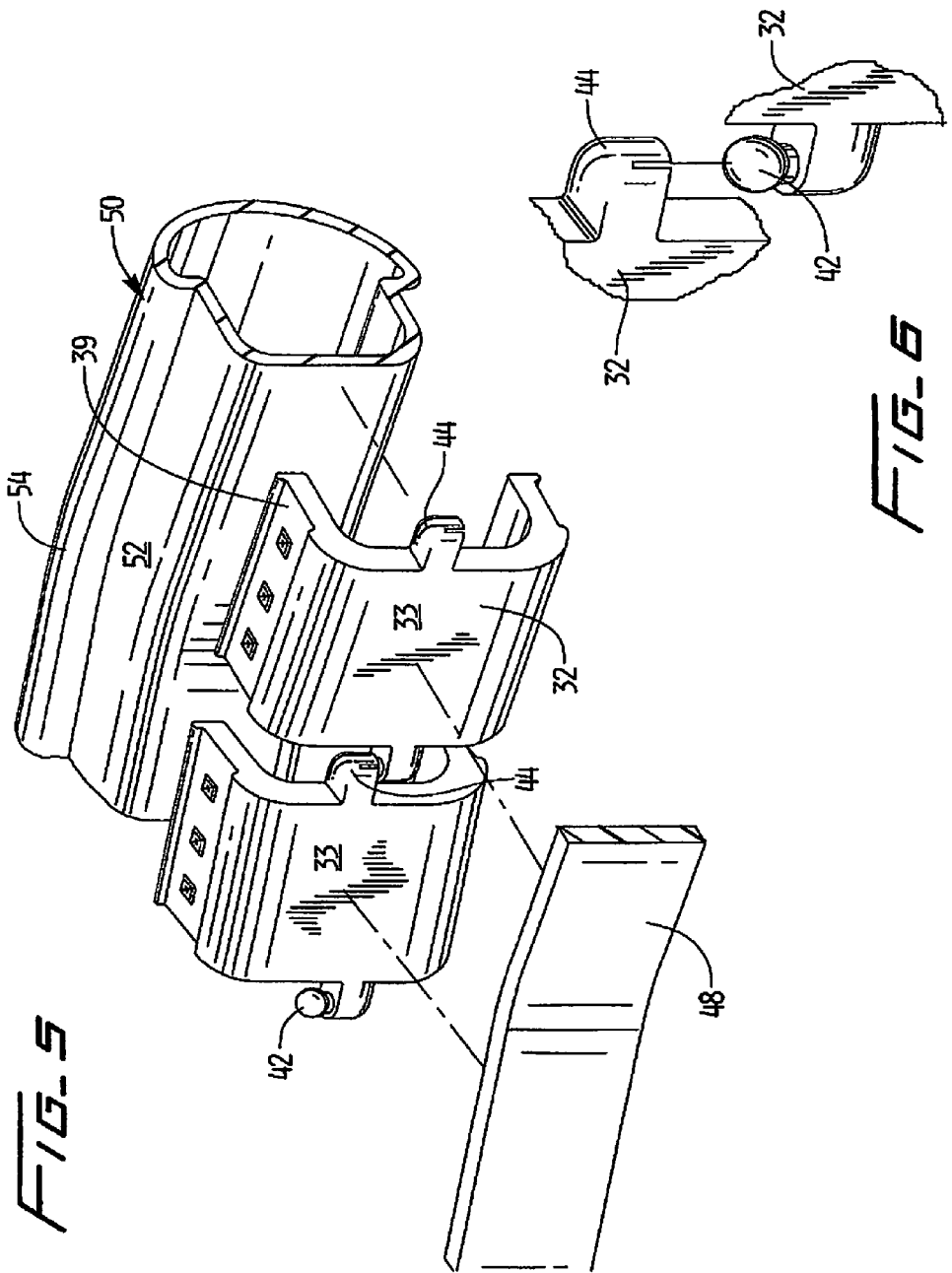

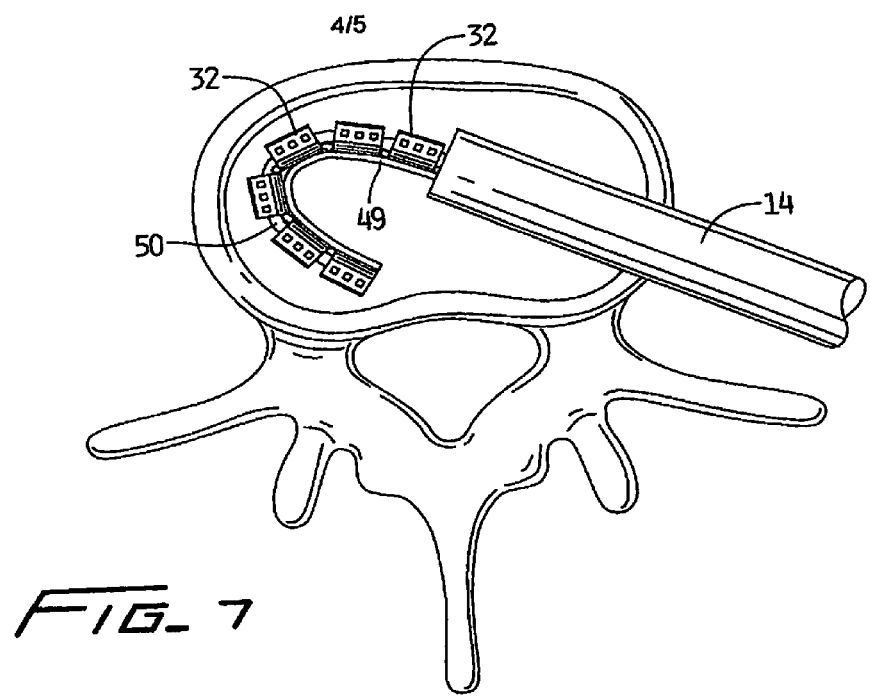
FIG_7
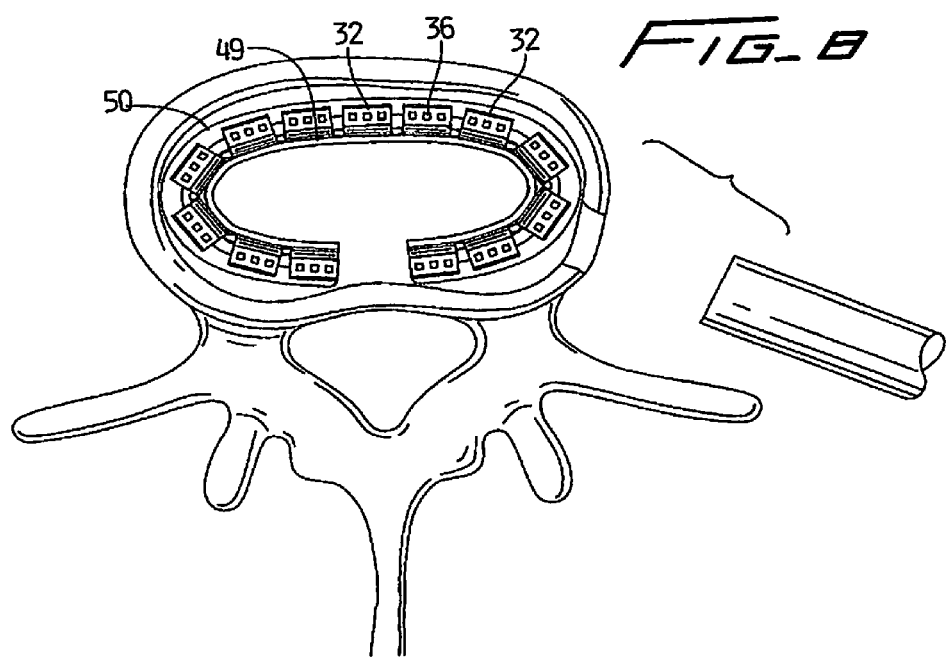
FIG_8

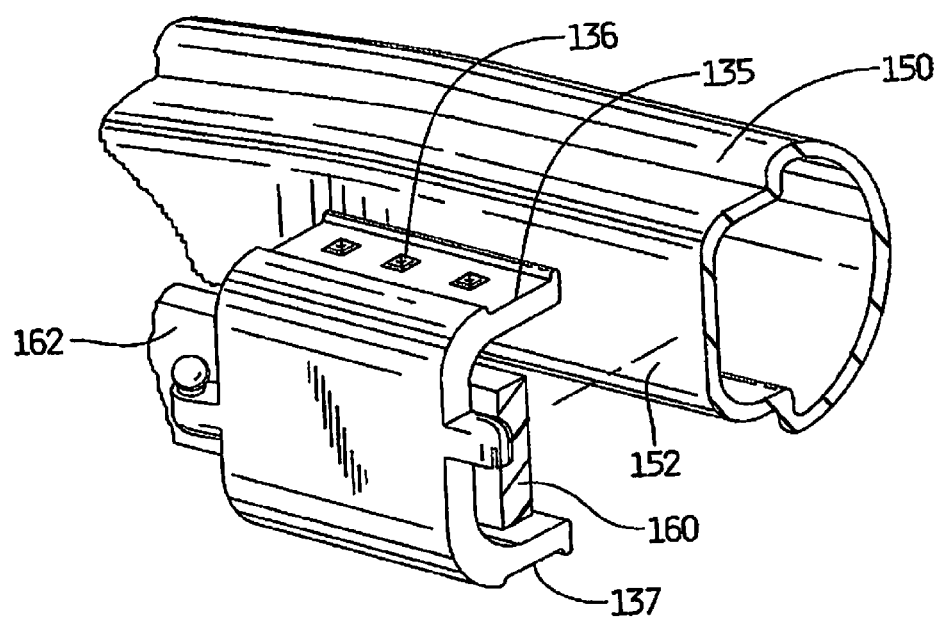
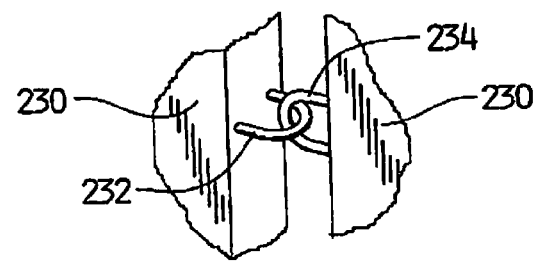

SPINAL IMPLANT AND METHOD OF USE

This application is a continuation of patent application Ser. No. 13/400,414, filed Feb. 20, 2012, which is a divisional of patent application Ser. No. 11/983,477, filed on Nov. 9, 2007, now U.S. Pat. No. 8,142,507, which claims priority from provisional application Ser. No. 60/859,357 filed Nov. 16, 2006. The entire contents of each of these applications are incorporated herein by reference.

BACKGROUND

1. Technical Field

This application relates to a spinal implant and more particularly to a spinal disc implant that can be inserted minimally invasively.

2. Background of Related Art

After removal of the intervertebral disc, it has been recognized that the disc space needs to be filled between the adjacent vertebrae. There are two approaches in the prior art to fill the space: one involving placement of a fusion cage and the other involving an artificial disc. Fusion cages are essentially metallic cages packed with bone to promote bone ingrowth. The fusion cages, designed to promote fusion, provide support between the vertebrae, but eliminate motion. Thus, to achieve stability, they sacrifice mobility.

Artificial disc prostheses of the prior art take many forms. Each form is essentially designed to strike a balance between sufficient stability to support the high loads of the vertebrae and sufficient mobility so as not to curtail movement of the patient. To date, attempts to strike such balance have met with limited success, with the artificial disc providing either stability or mobility, but not both. The need therefore exists for a disc replacement that can better simulate the natural disc by combining adequate support with flexibility.

Additionally, in many intervertebral procedures, major open surgery is required. The advantages of endoscopic (minimally invasive) procedures are well known, e.g. smaller incision causing less trauma and reduced infection potential, shorter hospital stays, lower costs, reduced patient recovery time, and reduced pain for the patient. Therefore, it would be advantageous if such an artificial disc, which achieves a beneficial balance between mobility and stability, could be inserted minimally invasively.

SUMMARY

The present invention provides a spinal implant having a series of sections or units hinged together and a balloon connected to at least some of the sections, the balloon having a curved configuration. The implant has a first delivery configuration and a second curved placement configuration, wherein it has a more linear configuration in the first delivery configuration than in the second curved configuration. The implant assumes the first delivery configuration during delivery to the disc space and maintains the curved configuration after placement within the disc space. The curved configuration can result from filling or expanding the balloon.

In one embodiment, a support strip is positioned on an outer surface of the hinged sections. In an alternate embodiment, it is positioned on the inner surface.

In the embodiment wherein a support strip is provided of shape memory material, the support strip can move the hinged sections to the curved configuration, and then the balloon filled to maintain the shape and support the sections. Alternatively, both the expanded balloon and support can together move the hinged sections to the curved configuration.

In one embodiment, the balloon in the expanded configuration has a first area and a smaller area having a smaller transverse cross section, each area extending along a length of the balloon.

The present invention also provides a method of minimally invasively inserting a spinal implant in a disc space. The method comprises providing a delivery instrument containing the spinal implant in a first configuration, the spinal implant having a plurality of hinged sections and a balloon connected thereto, inserting the delivery instrument to the disc space, deploying the implant from the delivery instrument to position the implant in the disc space, expanding the balloon to maintain the hinged sections in a substantially horseshoe shaped configuration, and removing the delivery instrument and leaving the implant in place.

In one embodiment the step of expanding the balloon expands the hinged section in a direction transverse to a plane of the disc space.

BRIEF DESCRIPTION OF THE DRAWINGS

Preferred embodiment(s) of the present disclosure are described herein with reference to the drawings wherein:

FIG. 1 is a perspective view of a cannula for receiving a disc removal device for use in the intra-vertebral space (the soft tissues are not shown);

FIG. 2 is a close up top view of the spinal disc nucleus being removed by a disc removal device;

FIG. 3 is a close up perspective view of a portion (two sections) of an implant device of the present invention;

FIG. 4 is a top plan view of the implant device of FIG. 3 shown in the curved deployed (placement) position;

FIG. 5 is an exploded view of the portion of the implant of FIG. 3;

FIG. 6 is a close up exploded view of the hinging element of the implant of FIGS. 3 and 4;

FIG. 7 is a plan view of the spinal implant of FIGS. 3 and 4 being delivered from the cannula of FIG. 1;

FIG. 8 is a top view of the implant of FIG. 4 shown in place between the vertebral bodies, the drawing further showing the cannula being removed;

FIG. 9 is an enlarged partially exploded view of an alternate embodiment of the implant of the present invention; and FIG. 10 is a close up perspective view of an alternate embodiment of a hinge for connecting adjacent implant sections.

DETAILED DESCRIPTION OF PREFERRED EMBODIMENTS

Referring now in detail to the drawings where like reference numerals identify similar or like components throughout the several views, several different embodiments of the spinal implant of the present invention are described herein.

The spinal implants of the present invention are designed to be inserted minimally invasively into the disc space, thus enabling a smaller incision to be used in the procedure. This is achieved by the implants being deflectable laterally to a substantially linear configuration. That is, the implant is in a more straightened shape to enable minimally invasive insertion through a cannula. Once ejected from the delivery instrument at the desired site, i.e. the disc space between adjacent vertebrae, the balloon will be filled and the implant maintained in a curved configuration. Implanted in the disc space, the spinal implant is radially compressible in response to vertebral loads placed thereon.

Turning first to the instrumentation for minimally invasively preparing the disc space and for minimally invasively delivering the spinal implant, and with initial reference to FIGS. 1 and 2, a device used in the intra-vertebral space to remove the spinal disc nucleus in a minimally invasive fashion is illustrated. The disc removal device 10 has an elongated tubular portion 12 which is inserted through an arthroscopic cannula 14 and has a pair of cutting jaws 16 which are operatively connected to and remotely manipulated, i.e. opened and closed, by a proximal handle (not shown) to cut and remove the disc nucleus. Insertion through arthroscopic cannula 14 enables the disc to be removed minimally invasively rather than through a larger incision during an open more invasive surgical procedure.

As the nucleus is removed endoscopically, i.e. through a cannula forming a small incision, the implant of the present invention that is designed to replace the removed disc is also advantageously inserted minimally invasively. A delivery instrument (not shown) containing the spinal implant 30 within a distal portion is inserted through cannula 14. Implant 30 is maintained in the delivery instrument in a substantially straightened (linear) configuration.

FIG. 7 illustrates the implant 30 partially ejected from the device; FIG. 8 illustrates the implant 30 fully deployed and implanted in the disc space. As can be appreciated, as the implant 30 is ejected it moves from its more straightened configuration toward its curved configuration described below. After placement of the implant 30, the delivery device and cannula are removed from the body.

As can be appreciated in the plan view of FIG. 8, the implant 30 is substantially horseshoe-shaped or substantially C-shaped in configuration as it extends circumferentially along the periphery of the disc space, thus providing support along the periphery or circumference of the disc space. That is, adjacent individual implant sections 32 are linked and form the curved shaped in a plane defined as lying perpendicular to the spine and parallel to the disc space defined between upper and lower vertebral bodies. It is also contemplated that the implant could be a closed loop, e.g. circular, or extend more than 360 degrees so the end portions overlap. In each of these instances, the implant would be delivered in a substantially straighter configuration and move to its curved shape for placement in the disc space.

With reference to FIGS. 3 and 4, the implant 30 is composed of a series of sections 32 linked together (only some of which are labeled for clarity). The linked sections 32 can be composed of a shape memory material, stainless steel, or other material to provide sufficient support. Each of these sections is preferably C-shaped or U-shaped in configuration with a lip 34 formed at the ends of its arms or upper and lower walls 35, 37. A textured surface such as protrusions 36 can be formed on the upper and lower surfaces 38, 39, respectively, of walls 35, 37 to increase surface friction between the implant and the opposing bone/vertebrae. Although protrusions are shown, other friction enhancing surfaces can be provided such as recesses, textured surfaces, different shaped projections and coatings. The walls 35, 37 can move toward each other due to the forces of the vertebral bodies between which it is inserted.

Adjacent sections 32 are hinged to enable movement from a more linear configuration for delivery through the cannula to the curved configuration shown in FIG. 4. FIG. 6 is an enlarged view of one embodiment of the hinged structure showing ball 42 received and snapped in a slot formed on the underside of connector 44. This frictional engagement interlocks adjacent sections 32 while still enabling lateral and pivotal movement with respect to one another.

A support or strut 48 illustratively in the form of an elongated flat strip is attached to the outer surface 33 of the hinged sections 32, preferably extending along the entire length. This strip 48 is preferably composed of metal and provides support for the hinged sections and assists in linking of the sections.

In one embodiment, the support is made of shape memory, such as Nitinol, a nickel titanium alloy, although other shape memory metals or polymeric materials are contemplated, and has a shape memorized configuration of a substantially horseshoe shape or substantially C-curve as shown in FIG. 4. In this manner, the support 48 is maintained in a substantially straightened configuration for delivery. Once ejected from the delivery device, it will move to its memorized configuration, cooperating with the balloon explained below to move the hinged sections 32 into the curved configuration of FIG. 4.

A balloon is designated by reference numeral 50 and shown in the inflated (filled) position in FIGS. 3-5. The balloon has a reduced diameter section 52 (see arrow D) along its length to fit within the open arms 35, 37 of the hinged sections 32. The balloon is substantially horseshoe shaped and functions to give the hinged sections the substantially horseshoe or curved shape shown in FIG. 4. The larger cross-section area 54 has a curved outer surface 56 and remains outside the hinged sections 32. A portion abuts lip 34. The balloon is filled with a gas or liquid after placement of implant 30 in the disc space to expand and extend in the curved configuration. The substantially horseshoe shape of the balloon thus forces the attached hinged sections 32 to form and/or maintain a curved shape, thereby providing the curved shape to the implant. The balloon 50 can also apply a force against the walls 35, 37 of the implant 30 (i.e. in a direction transverse to a plane of the disc space) and in some embodiments slightly expands these walls to further move surfaces 38, 39 against the vertebrae. The balloon materials and pressure can vary to thereby vary the degree of compressibility, cushioning and rigidity of the implant. That is, the variations of the balloon can affect the movement of adjacent vertebrae. For example, a less compressible balloon will increase stability but further restrict movement of the vertebrae; a more compressible balloon will provide more movement and mobility.

In the alternate embodiment of FIG. 9, the metal support strip 160, shown rectangular in cross section, is positioned inside the open arms 135, 137 of implant 130. The surface 152 of the balloon 150 is attached to the strip 160. The opposite surface 162 of the strip is attached to the inner surface of hinged sections 132. Metal strip 160 functions in a similar manner to strip 48 of FIG. 3.

FIG. 10 illustrates an alternate way to connect the implant units (sections) 230. Two engaging closed loops 232, 234 are linked to provide the attachment. This connection provides for movement of adjacent sections 230, while maintaining the inter-lock. It also helps to maintain the linked sections 32 in the curved configuration.

It is also contemplated that the support 48 (or 160) constitutes the element for moving the hinged sections to the curved configuration, with the balloon being moved to its curved shape by the hinged sections 32 and then maintaining the shape and support of the sections. Alternatively, the balloon can be the sole element moving the hinged sections 32 to the curved shape, with the support following the movement of the sections 32 to subsequently support the sections. Alternatively, both the balloon and support 48 (or 160) cooperate together to move and maintain the hinged sections.

Each of the implants assumes a substantially straightened configuration for delivery to the surgical site. Once delivered to the disc space, the hinged sections and the inflated balloon provide sufficient springiness in response to vertebral loads placed on the device by the spine. This provides both support for the vertebral bodies plus the desired flexibility. As noted above, variations in the balloon can vary the support and flexibility for the vertebral bodies.

Any of the foregoing implants can be provided with a roughened surface, such as a textured surface, to enhance bone ingrowth to enhance implant retention in the disc space. Surface finishes such as hydroxyapatite, calcium silicate and calcium phosphate could also be applied to allow for bone ingrowth.

In use, the disc nucleus is removed arthroscopically, i.e. through cannula 14, by device 10. Cannula 14 can optionally be placed by first inserting a needle and wire, removing the needle and sequentially placing and removing dilators of progressively increasing diameter over the wire until the desired cannula diameter is reached. After removal of the disc, device 10 is withdrawn through cannula 14 and then a delivery device, containing any of the foregoing implants, is inserted through the cannula. The implant is contained within the delivery device in a substantially straightened configuration with the balloon in the collapsed (unexpanded) configuration. The implant is then ejected from the delivery device and implanted in the disc space between the vertebral bodies, with the balloon filled to expand and maintain the curved configuration. The delivery instrument and cannula 14 are withdrawn from the body. FIG. 8 illustrates the implant 30 positioned within the disc space.

While the above description contains many specifics, those specifics should not be construed as limitations on the scope of the disclosure, but merely as exemplifications of preferred embodiments thereof. For example, in addition to the substantially C-shaped cross-sectional configurations, substantially circular, rectangular, hexagonal, substantially octagonal as well as other configurations are contemplated. Also the length of the implant could be longer than that shown in the drawings for assuming the curved shape. Those skilled in the art will envision many other possible variations that are within the scope and spirit of the disclosure as defined by the claims appended hereto.

What is claimed is:

1. A spinal implant for insertion through a cannula into a disc space between adjacent vertebrae, the spinal implant comprising a series of sections linked together and movable laterally with respect to each other, the series of linked sections movable from a more linear configuration for delivery through the cannula to a curved configuration when exposed from the cannula for placement circumferentially along a periphery of the disc space spaced from a central region of the disc space, to provide support along the periphery of the disc space, each of the linked sections having an upper wall and a lower wall, the upper and lower walls movable toward each other in response to forces applied by the adjacent vertebrae when the linked sections are placed in the disc space and an elongated support strip fixedly attached to the linked sections for delivery and placement with the linked sections, the support strip fully implantable with the linked sections in the disc space and fixedly attached to the linked sections during delivery of the implant and during placement of the implant, and upon delivery of the linked sections from the cannula the support strip moves from a substantially straightened configuration to a curved configuration as the linked sections move to the curved configuration.

2. The spinal implant of claim 1, wherein the linked sections are formed of shape memory material.

3. The spinal implant of claim 1, wherein the upper and lower walls have a friction enhancing surface.

4. The spinal implant of claim 3, wherein the friction enhancing surface is a textured surface.

5. The spinal implant of claim 1, wherein the support strip is composed of shape memory material.

6. The spinal implant of claim 1, wherein the support strip has a shape memorized configuration of a C-curve for implantation and is maintained in a substantially straightened configuration for delivery through the cannula.

7. The spinal implant of claim 1, wherein the support strip is a flat strip.

8. The spinal implant of claim 1, wherein the support strip is fixedly positioned outside the linked sections.

9. The spinal implant of claim 8, wherein the support strip is fixedly attached to an outer surface of the linked sections.

10. The spinal implant of claim 1, wherein the support strip is fixedly positioned inside the linked sections.

11. The spinal implant of claim 1, wherein the elongated support strip moves the linked sections to the curved configuration.

12. The spinal implant of claim 11, wherein the linked sections are composed of shape memory material.

13. The spinal implant of claim 1, wherein the linked sections are composed of a material to provide both flexibility and springiness in response to vertebral loads placed on the linked sections.

14. The spinal implant of claim 1, wherein each of the linked sections is C-shaped in cross-sectional configuration.

15. The spinal implant of claim 1, wherein the upper and lower walls each have a lip.

16. The spinal implant of claim 1, wherein the support strip extends along the entire length of the linked sections.

17. The spinal implant of claim 1, wherein a height of the support strip defined between upper and lower walls exceeds a width.

18. A spinal implant for insertion through a cannula into a disc space between adjacent vertebrae, the spinal implant comprising a series of sections linked together and movable laterally with respect to each other, the series of linked sections movable from a more linear configuration for delivery through the cannula to a curved configuration for placement circumferentially along a periphery of the disc space spaced from a central region of the disc space to provide support along the periphery of the disc space, each of the linked sections having an upper wall and a lower wall, the upper and lower walls movable toward each other in response to forces applied by the adjacent vertebrae when the linked sections are placed in the disc space, and an elongated support strip fixedly attached to the linked sections during delivery and during placement of the linked sections, the support strip having a height and a width, the height defined between top and bottom walls, the height defining a first wall which extends along a second wall of the linked sections defined between the upper and lower walls of the linked sections, wherein upon delivery of the linked sections from the cannula, the support strip moves from a substantially straightened configuration to the curved configuration as the linked sections move to the curved configuration.

19. The spinal implant of claim 18, wherein the support strip extends along an outer surface of the second wall.

20. The spinal implant of claim 18, wherein the support strip extends along an inner surface of the second wall.

* * * * *